United States Patent
Shen et al.

(12) 
(10) Patent No.: US 6,819,417 B1
(45) Date of Patent: Nov. 16, 2004

(54) IN-LINE MONITORING OF SILICIDE QUALITY USING NON-DESTRUCTIVE METHODS

(75) Inventors: Yun-Hung Shen, Hsinchu (TW); Bih-Huey Lee, Hsinchu (TW)

(73) Assignee: Taiwan Semiconductor Manufacturing Co., Ltd, Hsin-Chu (TW)

(*) Notice: Subject to any disclaimer, the term of this patent is extended or adjusted under 35 U.S.C. 154(b) by 161 days.

(21) Appl. No.: 10/140,648

(22) Filed: May 7, 2002

(51) Int. Cl.[7] .............................................. G01N 21/88
(52) U.S. Cl. ..................... 356/237.4; 356/128; 438/630
(58) Field of Search .............. 356/237.1, 237.2–237.5, 356/128, 630; 438/630, 649, 651, 664, 682

(56) References Cited

U.S. PATENT DOCUMENTS

| | | | | |
|---|---|---|---|---|
| 4,188,123 A | * | 2/1980 | Kleinknecht | 356/521 |
| 5,042,952 A | | 8/1991 | Opsal et al. | 356/432 |
| 5,321,264 A | | 6/1994 | Kuwabara et al. | 250/339.01 |
| 5,578,161 A | | 11/1996 | Auda | 156/626.1 |
| 6,052,185 A | | 4/2000 | Banet et al. | 356/345 |
| 6,141,103 A | | 10/2000 | Pinaton et al. | 356/369 |
| 6,376,343 B1 | * | 4/2002 | Buynoski et al. | 438/529 |

* cited by examiner

Primary Examiner—Richard A. Rosenberger
Assistant Examiner—Vincent P. Barth

(57) ABSTRACT

A new method is provided for monitoring silicon quality, the new method is applied at the time of pre-salicidation of the silicon substrate. The optical refractive index of the pre-salicide substrate is monitored, this monitoring provides insight into the quality of the silicon substrate at that time of a substrate processing cycle.

28 Claims, 3 Drawing Sheets

IN-LINE MONITORING OF SILICIDE QUALITY USING NON-DESTRUCTIVE METHODS

BACKGROUND OF THE INVENTION (1) Field of the Invention

The invention relates to the fabrication of integrated circuit devices, and more particularly, to a method of monitoring the quality of silicided surfaces.

(2) Description of the Prior Art

The creation of semiconductor devices applies various techniques such as creating surface regions of different conductivity by impurity ion implantation, the growth of overlying layers of epitaxy and the diffusion of implanted impurity ions. All of these techniques have specific objectives such as creating regions of conductivity or the establishment of low-resistivity contact regions to semiconductor devices. This latter approach is notably used in establishing contact surfaces to points of contact of CMOS devices. A CMOS device in it simplest form comprises a gate electrode with impurity ion implantations having been provided into the surface of the substrate over which the gate electrode is created. Contact plugs are provided to the source/drain regions of the gate electrode and to the surface of the gate electrode. Where these contact plugs interface with the contacted regions, special surface interfaces are provided to assure a low-resistivity interface, optimizing device performance.

FIG. 1 shows a cross section of a conventional CMOS device, the creation of this device will be briefly highlighted using the device elements that are highlighted in FIG. 1. The process of creating a CMOS device starts by providing a semiconductor substrate 10, FIG. 1. Insulation regions 12, that bound the active region in the surface of substrate 10, isolate the active region and may comprise regions of Field Oxide (FOX) isolation or Shallow Trench Isolation (STI). A thin layer 14 of gate oxide is grown over the surface of the substrate 10 in the active device region. To create the gate structure, a layer 16 of polysilicon is grown over the thin layer 14 of gate oxide. The polysilicon layer 16 is masked and the exposed polysilicon 16 and the thin layer 14 of oxide are etched to create the polysilicon gate 16 that is separated from the substrate 10 by the remaining thin layer 14 of oxide. The doping of the source/drain regions starts with creating the lightly N+ doped diffusion (LDD) regions 11. The sidewall spacers 24 for the gate structure are formed after which the source (13) and drain (15) regions doping is completed by doping the source/drain regions 13/15 to the desired level of conductivity using an impurity implantation.

Low resistivity contact point 18 to the source (13) and contact point 20 to the drain (15) regions and contact point 22 to the electrode gate (16) are then formed by first depositing a layer of for instance titanium over the surface of the source/drain regions and the top surface of the gate electrode. This titanium is annealed, causing the deposited titanium to react with the underlying silicon of the source/gain regions and the doped surface of the gate electrode. This anneal forms layers of titanium silicide 18/20 on the surfaces of the source/drain regions 13/15 and layer 22 on the top surface of the gate electrode 16.

Metal contact 28 with the source (13) region, metal contact 30 with the drain (15) region and metal contact 32 with the gate electrode (16) are formed as a final step. A layer 26 of dielectric, such as silicon oxide, is blanket deposited over the surface of the created structure. This layer of dielectric is patterned and etched to create contact openings 27/29 over the source/drain regions 13/15 and opening 31 over the top surface of the gate electrode 16. A metallization layer is deposited over the patterned layer 26 of dielectric, establishing the electrical contacts 28/30 with the source/drain regions 13/15 and 32 with the top surface of the gate electrode 16.

The invention addresses concerns of damage that occurs to the surface of the source/drain regions during processing steps of plasma wet etching, which are required for the etching of gate spacers 24 and which are required for the creation of openings 27/29 through the layer 26 of dielectric. The quality of the silicided surface 18/20 degrades as a consequence of these plasma etching procedures, resulting in reduced molecular smoothness of these surface (that is: poor surface morphology) and in high sheet resistance of the surfaces of layers 18/20.

U.S. Pat. No. 6,141,103 (Pinaton et al.) shows a method using refractive index to monitor an I/I process.

U.S. Pat. No. 61,052,185 (Banet et al.) reveals a method using a laser to determine concentrations in wafers.

U.S. Pat. No. 5,578,161 (Auda) discloses a method to monitor trenches using spectrometers.

U.S. Pat. No. 5,321,264 (Kuwabara et al.) and U.S. Pat. No. 5,042,952 (Opsal et al.) show methods to measure wafer surface properties using Index of refraction and other methods.

SUMMARY OF THE INVENTION

A principle objective of the invention is to monitor and thus remove the potential for damage to the source/drain surface regions of a silicon substrate during plasma etching.

Another objective of the invention is to monitor and thereby prevent a negative impact on the silicon surface of a silicon substrate during plasma etching.

Yet another objective of the invention is to prevent a negative impact surface morphology of a silicon substrate during plasma etching.

Another objective of the invention is to monitor and thereby prevent a negative impact on the silicon surface of a silicon substrate during impurity implantations.

In accordance with the objectives of the invention a new method is provided for monitoring silicon quality, the new method is applied at the time of pre-salicidation of the silicon substrate. The optical refractive index of the pre-salicide substrate is monitored, this monitoring provides insight into the quality of the silicon substrate at that time of a substrate processing cycle.

DESCRIPTION OF THE PREFERRED EMBODIMENTS

Figure 1:
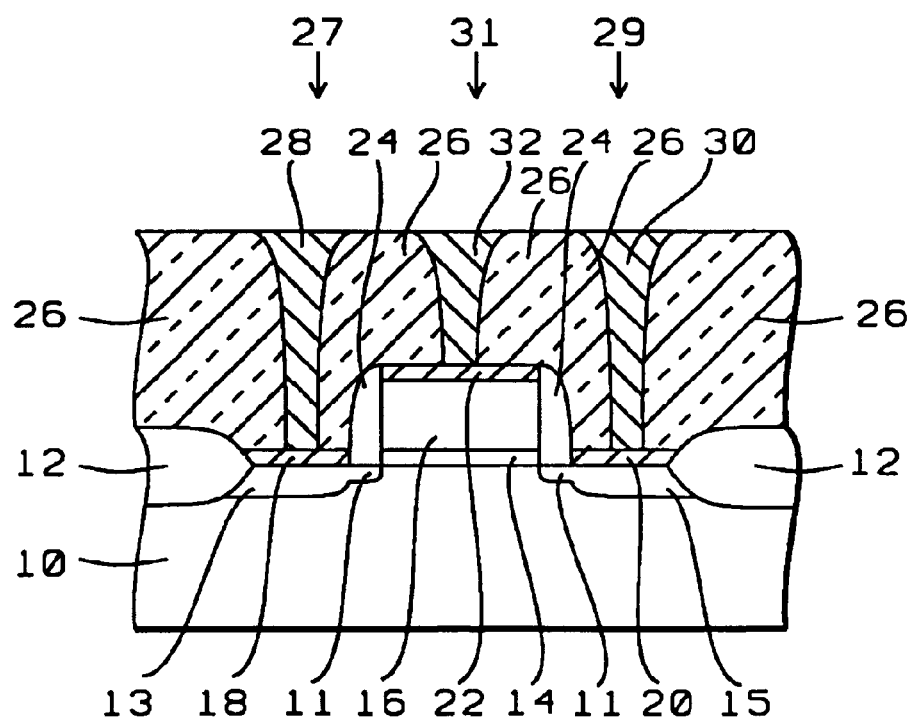
FIG. 1 shows a cross section of a prior art gate electrode and the elements that comprise such a semiconductor device.

The use of self-aligned salicidation has been highlighted above using prior art FIG. 1. It is further well known in the art that the process of salicidation is enhanced by doping the surface of the silicon region on which the salicide formation is to occur. This doping is known as Pre-Amorphization Implantation (PAI), which is widely used for sub-micron devices with device dimensions of about 0.25 μm. During the process of PAI, gate electrode structures that are not subjected to the PAI implant are shielded from the implant by an overlying photoresist mask. A layer of Resist Protective Oxide (RPO) is first deposited over the surface of the gate electrodes and is then removed from above the gate electrodes to which the PAI has to be performed. The etch of the layer of RPO exposes the surface of the silicon substrate around gate electrodes that are to be subjected to the PAI, potentially having a detrimental effect on the surface quality of the surface overlying the source/drain regions of these gate electrodes.

It is well known in the art that monitoring methods can be applied to the surface of a silicon substrate that is being processed, whereby the monitoring methods comprise monitoring surface characteristics of the substrate that is being processed. For instance, U.S. Pat. No. 5,042,952 (Opsal et al.) provides for a method and apparatus for evaluating surface and subsurface features in a semiconductor sample. This patent makes use of the fact that, in operation, a periodic energy source is applied to the surface of a semiconductor sample to generate periodic electron-hole plasma. This plasma interacts with features in the sample as it diffuses. The plasma then affects the index of refraction of the sample and the changing plasma density is monitored using a radiation probe. In the preferred embodiment of this invention, the radiation probe measures the plasma induced periodic changes of reflectivity of the surface of the sample to yield information about the sample, such as ion dopant concentration, residue deposits and defects.

Similar methods have been provided in the above referred to methods. The invention provides as yet another method whereby non-destructive testing of a substrate surface can be applied by monitoring the optical refractive index of the surface of the substrate. This method is applied prior to the salicidation of the surface of the substrate for the formation of salicided contact regions.

From extensive observations that relate to and form the basis for the invention, the following operational aspects have been derived:
1. the optical refractive index of the silicon substrate can be correlated with the sheet resistance of the silicided layer that is formed over the surface of the substrate
2. the optical refractive index of the silicon substrate can be correlated with the morphology of the silicided layer that is formed over the surface of the substrate
3. the optical refractive index of the silicon substrate can be correlated with the plasma damage of the silicided layer that is formed over the surface of the substrate
4. the optical refractive index of the silicon substrate cannot be correlated with the ion implant conditions of the silicided layer that is formed over the surface of the substrate, and
5. the latter two points enable to make a clear distinction between plasma damage and ion implant conditions since monitoring the latter ion implant conditions does not affect and is not part of the invention.

Further detail which highlight experimental results that relate to the invention are presented next. The method of the invention relates to and is limited to the formation of titanium (Ti) based salicided surface.

The processing sequence that is part of the experiment must first be highlighted, impurity implantations into the surface of the substrate (LDD and source/drain) are not highlighted as part of this sequence since these implantations have no influence on the invention, as follows:
a silicon substrate is provided, a gate electrode structure overlying a layer of gate oxide is formed over the surface of the substrate
gate spacers are forming over sidewalls of the gate electrode; during the formation of the gate spacers, the surface of the silicon substrate may be attacked by the etch that is required for the creation of the gate spacers; the invention monitors this aspect of gate structure formation, that is the effect that the gate spacer etch has on the surface of the silicon substrate over which contact points (salicided surfaces) to the source/drain regions of the gate electrode are to be formed; if the plasma damage exceeds a certain boundary (that is: is high enough), the subsequently formed layer of titanium silicide over the surfaces of the source/drain regions are of poor quality, causing high contact resistance to the source and drain regions of the gate electrode.

For experimental purposes, at least two silicon substrates are provided, a layer of titanium silicide is formed over the surface of the substrate, a layer of dielectric is created over the surface of the substrate, an opening is etched through the layer of dielectric, exposing the surface of the layer of titanium silicide. Since the experiment started with at least two silicon substrate, the possibility is introduced that these two silicon substrates have different surface qualities that may result in the creation of different layers of titanium silicide over the surface thereof.

The invention has used the following parameters to derive related conclusions:
surface quality of the surface of the silicon substrate and as expressed in the optical refractive index of the intrinsic silicon substrate
the thickness of the layer of $TiSi_2$ that is created over the surface of the substrate
correlating the thickness of the layer of $TiSi_2$ that is created over the surface of the substrate with the optical refractive index of the intrinsic silicon substrate. Following these steps of experiment, the invention has found that:
1. the value of the optical refractive index of the intrinsic silicon substrate just before the deposition of the layer of titanium over the surface of the silicon substrate is indicative of and correlates with the quality of the formed layer of $TiSi_2$
2. more extensive plasma damage to the surface of the silicon substrate leads to a higher value of the optical refractive index (n) of the silicon surface, and
3. higher value of "n" corresponds with a higher value of sheet resistance of the created layer of $TiSi_2$.

This has been confirmed by analyzing the thickness of the layer of $TiSi_2$ at the bottom of the opening created through the layer of dielectric, this thickness of the layer of $TiSi_2$ has been correlated with the optical refractive index (n) of the silicon surface.

Experiments that have been performed with the objective of determining poor contact resistance of source/drain surfaces that are formed of $TiSi_2$ can be summarized as follows using the above highlighted sequence of:
providing more than one silicon substrate
measuring the optical refractive index (n) of the silicon surface for each silicon substrate
forming a layer of $TiSi_2$ over the surface of the substrate depositing a layer of dielectric over the layer of TiSi$_2$ etching an opening through the layer of dielectric establishing a contact plug through the opening created through the layer of dielectric, and measuring the contact resistance of the contact plug.

By using a multitude of silicon substrates, a range of values of the optical refractive index is obtained, which allows for comparing this range of values of the optical refractive index (n) with the measured contact resistance of the contact plug.

As one of the results that has been obtained in this manner can be cited that a first layer of TiSi$_2$, created over a first silicon substrate by following the above highlighted sequence of processing steps, has a measured thickness of about 100 Angstrom. A second layer of TiSi$_2$, created over a second silicon substrate by following the identical above highlighted sequence of processing steps, has a measured thickness of about 400 Angstrom.

The identifiable difference between the first layer of TiSi$_2$ and the second layer of TiSi$_2$ is that the first layer of TiSi$_2$ has been formed over a silicon substrate having a low optical refractive index while the second layer of TiSi$_2$ has been formed over a silicon substrate having a high optical refractive index. From this may be concluded that the value of the optical refractive index can be used as an indicator of the thickness, and with that the quality or sheet resistance, of the layer of TiSi$_2$ that is formed over the silicon surface.

Specifically:

with an optical refractive index of the intrinsic silicon substrate within the range between about 3.82 and 3.85, the silicide quality, that is the morphology and the sheet resistance, of the created layer of TiSi$_2$ is acceptable with an optical refractive index of the intrinsic silicon substrate that is larger than 3.89, the silicide quality is poor.

Figure 2:
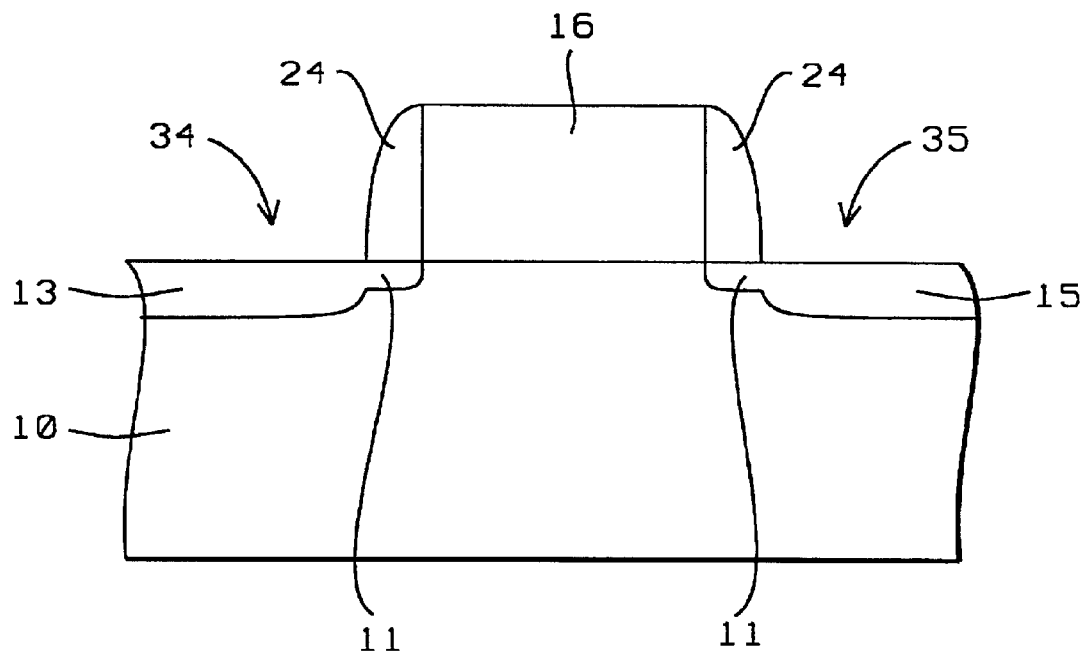
FIGS. 2 and 3 show a cross section of a gate electrode structure for purposes of demonstrating the formation of salicided surfaces for this structure.

FIG. 2 shows a cross section of a gate electrode structure whereby gate spacers 24 have been formed by applying a plasma etch. Gate spacers are typically created using such materials as PSG, polysilicon, other materials preferably of a dielectric nature, CVD oxide formed from a TEOS source, amorphous materials that inhibit the deposition of epitaxial silicon thereupon.

A layer of gate spacer material can be formed using thermal or CVD S$_i$N or using thermal or CVD SiO$_x$N$_y$, created to a thickness within the range between 250 and 1500 Angstrom.

As an example of creating silicon oxide gate spacers can be cited using an anisotropic RIE of a deposited layer of silicon oxide layer, using CHF$_3$ or CF$_4$—O$_2$—He as an etchant.

As an example of creating silicon nitride gate spacers can be cited using an anisotropic RIE of a deposited layer of silicon nitride layer, using CHF$_3$ or SF$_6$—O$_2$ as an etchant.

The elements that have been highlighted in FIG. 2 have previously been explained, FIG. 2 highlights that the surface areas 34 and 35, respectively over the source and drain regions 13/15 of the gate electrode, are exposed to the gate spacer etch and can therefore be damaged during this etch. A damaged surface of the source/drain regions will result in high contact resistance to these regions.

Figure 3:
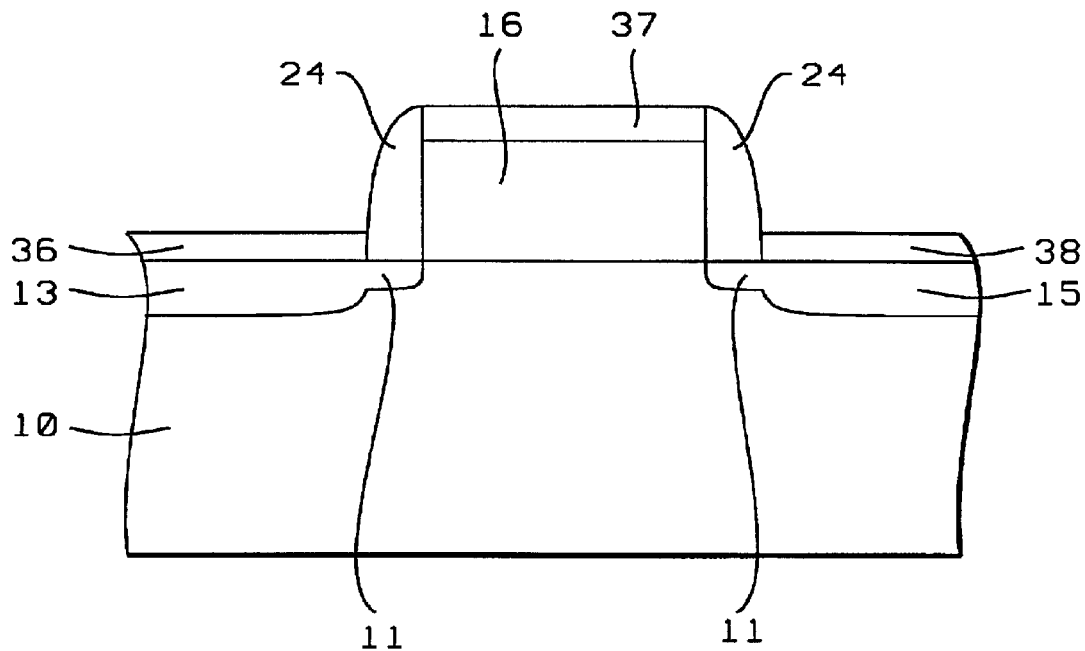

FIG. 3 shows a cross section of the gate structure after the layers 36, 37 and 38 of TiSi$_2$ have been formed over the contact surfaces of the gate electrode. By, as highlighted in detail above, measuring the optical refractive factor of the surfaces 34 and 35, FIG. 2, before deposition of the layer of titanium for the formation of the layers 36 and 38, FIG. 3, of TiSi$_2$ the contact resistance and the morphology of the created layers 36 and 38 can be predicted.

Figure 4:
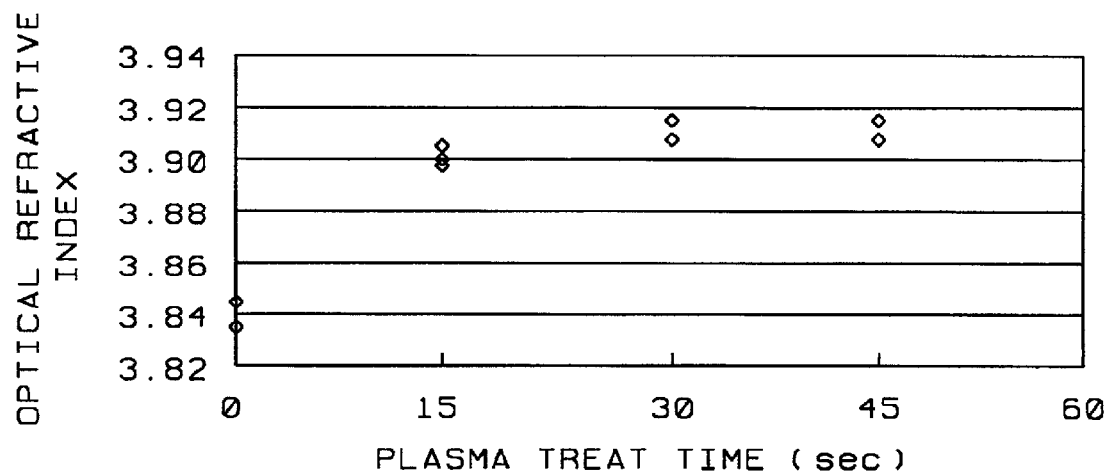
FIG. 4 shows the correlation between the optical refractive index of a silicon surface and the time of exposure of this surface to a plasma treatment.
Figure 5:
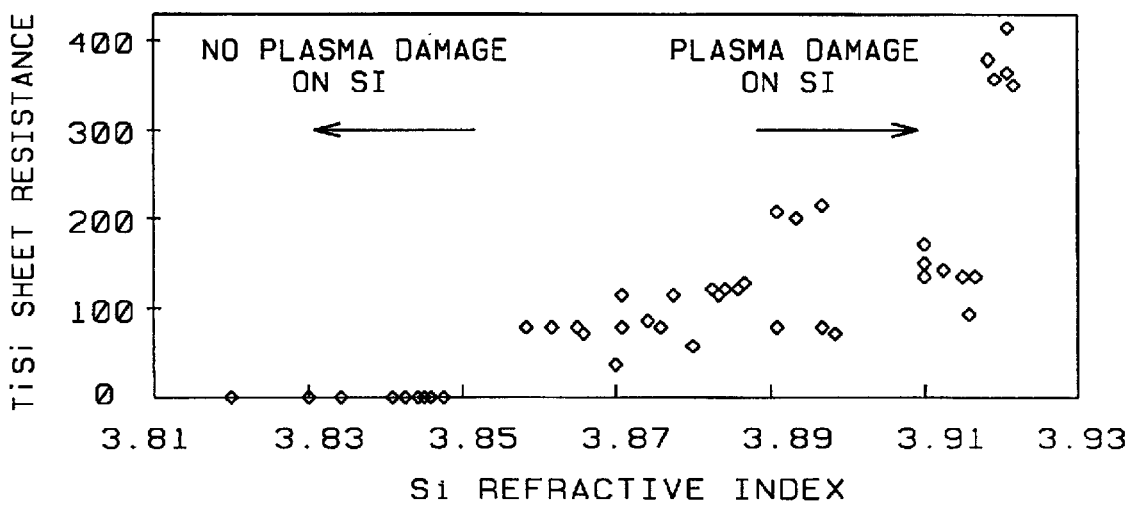
FIG. 5 shows the correlation between titanium silicide sheet resistance and the optical refractive index of a silicon surface over which the layer of titanium silicide is formed.

Further experimental results are shown in FIGS. 4 and 5. FIG. 4 shows the silicon refractive index versus plasma treat exposure time. From FIG. 4 the following can be concluded:

the optical refractive index of the silicon surface has a relatively low value of about 3.84 prior to plasma exposure of the silicon surface the refractive index of the silicon surface increases after plasma exposure of the surface; it is believed that the dielectric constant ($\in$) of the surface of the silicon substrate increases during plasma exposure due to the formation of electrical dipoles in the surface of the silicon substrate with silicon bonds; the optical refractive index is proportional to the square root of the dielectric constant ($\in^{1/2}$), therefore the optical refractive index increases with increased plasma exposure or increased silicon surface damage, and the value of the optical refractive index saturates at about 3.92, even if the plasma exposure is further extended; this is believed to be due to the protection that is provided by the plasma-enhance polymer, which blocks ion damage after the first few seconds of plasma treatment.

FIG. 5 shows the TiSi$_2$ sheet resistance versus the silicon optical refractive index. It is clear from the depiction of FIG. 5 that:

FIG. 5 further highlights plasma damage caused by exposure of a silicon surface to a plasma etch as this plasma damage relates to the measured silicon optical refractive index.

FIG. 4 shows, as highlighted above, that prior to plasma exposure of a silicon surface, an optical refractive index of about 3.84 is measured for the silicon surface. Increased values of the optical refractive index, which exceed a value of about 3.84, which are observed to occur as a result of plasma exposure of the silicon surface and which are shown alone the vertical or Y-axis of FIG. 4, result in (as highlighted above) increased contact resistance of the silicon surface or a there-over created point of contact, due to increased damage of the silicon surface caused by the exposure of the silicon surface to a plasma etch.

This is highlighted in the top left and right-hand corners of FIG. 5, that is: —a silicon optical refractive index of about 3.84, shown in the vertical or Y-axis of FIG. 4 and on the horizontal or X-axis of FIG. 5, is indicative of no plasma treat time and therefore no plasma damage to the silicon surface, as shown in the left hand upper corner of FIG. 5 —a silicon optical refractive index higher than about 3.84, shown in the vertical or Y-axis of FIG. 4 and on the horizontal or X-axis of FIG. 5, is indicative of the silicon surface being exposed to a plasma etch (the plasma treat time increases. FIG. 4) and therefore the introduction of plasma damage to the silicon surface, as shown in the right hand upper corner of FIG. 5.

higher values of sheet resistance correspond with higher values of the optical refractive index for a value of the optical refractive index within the range of about 3.82 and 3.85, the sheet resistance is about 2 to 3 Ohm for a value of the optical refractive index that exceeds about 3.89, the value for the sheet resistance exceeds about 100 Ohm, and a damaged substrate leads to poor silicide formation.

As an additional source of damage that can be caused to the surface of a silicon substrate can be identified impurity implantations such as source and drain region implantations into the surface of a silicon substrate. The surface of the source and drain regions are frequently, for previously stated reasons of improved contact resistance performance, silicided, raising concerns of the quality of the surface of the silicon substrate after the completion of the impurity implantations and prior to the salicidation process of these surface regions. The highlighted method of the invention can be equally applied for these applications of source/drain implantations followed by salicidation of the surface thereof.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications which fall within the scope of the appended claims and equivalents thereof.

What is claimed is:

1. A method for in-line monitoring of silicide quality, using a non-destructive method, comprising:
   providing a silicon substrate;
   monitoring an optical refractive index of the silicon substrate;
   creating a silicided layer over said silicon substrate dependent at least in part on conditions of optical refractive index of said silicon substrate.

2. The method of claim 1, said conditions of optical refractive index comprising an optical refractive index between about 3.82 and 3.85.

3. The method of claim 1, said silicided layer comprising $TiSi_2$.

4. A method for in-line monitoring of silicide quality, using a non-destructive method, comprising:
   providing a silicon substrate;
   monitoring an optical refractive index of the silicon substrate;
   creating a silicided layer over said silicon substrate for conditions of optical refractive index of said silicon substrate between about 3.82 and 3.85.

5. The method of claim 4, said silicided layer comprising $TiSi_2$.

6. A method for in-line monitoring of silicide quality, using a non-destructive method, comprising:
   providing a silicon substrate;
   monitoring an optical refractive index of the silicon substrate;
   creating a silicided layer comprising $TiSi_2$ over said silicon substrate for conditions of optical refractive index of said silicon substrate, said conditions of optical refractive index comprising a value of said optical refractive index between about 3.82 and 3.85.

7. A method for in-line monitoring of silicide quality, using a non-destructive method, comprising:
   providing a silicon substrate;
   monitoring an optical refractive index of the silicon substrate;
   rejecting creation of a silicided layer over said silicon substrate dependent at least in part on conditions of optical refractive index of said silicon substrate being larger than a minimum limit.

8. The method of claim 7, said minimum limit being about 3.89.

9. The method of claim 7, said silicided layer comprising $TiSi_2$.

10. A method for in-line monitoring of silicide quality, using a non-destructive method, comprising:
    providing a silicon substrate;
    monitoring an optical refractive index of area of the silicon substrate;
    rejecting creation of a silicided layer over said silicon substrate for conditions of optical refractive index of said silicon substrate being larger than about 3.89.

11. The method of claim 10, said silicided layer comprising $TiSi_2$.

12. A method for in-line monitoring of silicide quality, using a non-destructive method, comprising:
    providing a silicon substrate;
    monitoring an optical refractive index of the silicon substrate;
    rejecting creation of a silicided layer comprising $TiSi_2$ over silicon substrate for conditions of optical refractive index of said silicon substrate being larger than about 3.89.

13. A method for in-line monitoring of sheet resistance of a silicided surface, using a non-destructive method, comprising:
    providing a silicon substrate;
    monitoring an optical refractive index of the silicon substrate;
    creating a silicided layer over said silicon substrate dependent at least in part on conditions of optical refractive index of said silicon substrate.

14. The method of claim 13, said conditions of optical refractive index comprising an optical refractive index being between about 3.82 and 3.85.

15. The method of claim 13, said silicided layer comprising $TiSi_2$.

16. A method for in-line monitoring of sheet resistance of a silicided surface, using a non-destructive method, comprising:
    providing a silicon substrate;
    monitoring an optical refractive index of the silicon substrate;
    creating a silicided layer over said silicon substrate for conditions of optical refractive index of said silicon substrate between about 3.82 and 3.85.

17. The method of claim 16, said silicided layer comprising $TiSi_2$.

18. A method for in-line monitoring of sheet resistance of a silicided surface, using a non-destructive method, comprising:
    providing a silicon substrate;
    monitoring an optical refractive index of the silicon substrate;
    creating a silicided layer comprising $TiSi_2$ over said silicon substrate for conditions of optical refractive index of said silicon substrate being between about 3.82 and 3.85 of said surface area.

19. A method for in-line monitoring of sheet resistance of a silicided surface, using a non-destructive method, comprising:
    providing a silicon substrate;
    monitoring an optical refractive index of the silicon substrate;
    rejecting creation of a silicided layer over said silicon substrate dependent at least in part on conditions of optical refractive index of said silicon substrate.

20. The method of claim 19, said conditions of optical refractive index comprising an optical refractive index of at least about 3.89.

21. The method of claim 19, said silicided layer comprising $TiSi_2$.

22. A method for in-line monitoring of sheet resistance of a silicided surface, using a non-destructive method, comprising:

provicing a silicon substrate;

monitoring an optical refractive index of the silicon substrate;

rejecting creation of a silicided layer over said silicon substrate for conditions of optical refractive index of said silicon substrate being larger than about 3.89.

23. The method of claim 22, said silicided layer comprising $TiSi_2$.

24. A method for in-line monitoring of sheet resistance of a silicided surface, using a non-destructive method, comprising:

providing a silicon substrate;

monitoring an optical refractive index of the silicon substrate;

rejecting creation of a silicided layer comprising $TiSi_2$ over said silicon substrate for conditions of optical refractive index of said silicon substrate being larger than about 3.89.

25. A method of monitoring sheet resistance of a silicided layer that is formed over a substrate by correlating said sheet resistance with an optical refractive index of a surface over which said silicided layer is formed, a high value of about 3.89 or larger of said optical refractive index being indicative of a high sheet resistance, a low value of between about 3.84 and 3.89 of said refractive index being indicative of a low sheet resistance.

26. A method of monitoring morphology of a silicided layer that is formed over a substrate by correlating said morphology with an optical refractive index of a surface over which said silicided layer is formed, a high value of about 3.89 or larger of said optical refractive index being indicative of a high level of morphology, a low value of between about 3.84 and 3.89 of said refractive index being indicative of a low level of morphology.

27. A method of monitoring plasma damage of a substrate over which a silicided layer is formed by correlating said plasma damage with an optical refractive index of the substrate, a high value of about 3.89 or larger of said optical refractive index being indicative of a high degree of plasma damage, a low value of between about 3.84 and 3.89 of said refractive index being indicative of a low degree of plasma damage.

28. A method of monitoring surface damage caused by impurity implantations into a substrate over which a silicided layer is formed by correlating said impurity implantations with an optical refractive index of the substrate, a high value of about 3.89 or larger of said optical refractive index being indicative of a high degree of surfaced damage due to impurity implantations, a low value of between about 3.84 and 3.89 of said refractive index being indicative of a low degree of surface damage due to impurity implantations.

* * * * *

UNITED STATES PATENT AND TRADEMARK OFFICE
CERTIFICATE OF CORRECTION

PATENT NO. : 6,819,417 B1
DATED : November 16, 2004
INVENTOR(S) : Yun-Hung Shen and Bih-Huey Lee It is certified that error appears in the above-identified patent and that said Letters Patent is hereby corrected as shown below:

Column 6,
Lines 56 through 64, move the following text to Column 6, line 27, after the word "that":
-- higher values of sheet resistance correspond with higher values of the optical refractive index
for a value of the optical refrative index within the range of about 3.82 and 3.85, the sheet resistance is about 2 to 3 Ohm
for a value of the optical refractive index that exceeds about 3.89, the value for the sheet resistance exceeds about 100 Ohm, and
a damaged substrate leads to poor silicide formation. --

Signed and Sealed this

Twenty-sixth Day of April, 2005

JON W. DUDAS
*Director of the United States Patent and Trademark Office*